(12) United States Patent
McDevitt et al.

(10) Patent No.: US 6,536,448 B2
(45) Date of Patent: Mar. 25, 2003

(54) HEMOSTAT COATED DENTAL FLOSS AND HEMOSTAT COATED DENTAL TAPE

(75) Inventors: Jason Patrick McDevitt, Alpharetta, GA (US); Sohail Malik, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/752,423

(22) Filed: Dec. 29, 2000

(65) Prior Publication Data

US 2002/0083955 A1 Jul. 4, 2002

(51) Int. Cl.⁷ .................................................. A61C 15/00

(52) U.S. Cl. ....................................... 132/321; 132/329

(58) Field of Search ................................ 132/321, 320, 132/323, 325, 327, 326, 328, 329; 424/49, 50, 52

(56) References Cited

U.S. PATENT DOCUMENTS

| 3,771,536 | A | | 11/1973 | Dragan | 132/321 |
| 3,800,812 | A | | 4/1974 | Jaffe | 132/312 |
| 3,830,246 | A | | 8/1974 | Gillings | 132/321 |
| 3,897,795 | A | | 8/1975 | Engel | 132/321 |
| 3,943,949 | A | | 3/1976 | Ashton et al. | 132/321 |
| 4,033,365 | A | | 7/1977 | Klepak et al. | 132/321 |
| 4,215,478 | A | | 8/1980 | Thomas et al. | 132/321 |
| 5,209,251 | A | | 5/1993 | Curtis et al. | 132/321 |
| 5,711,938 | A | | 1/1998 | Larm | 132/321 |
| 5,891,422 | A | | 4/1999 | Pan et al. | 424/49 |
| 5,908,039 | A | * | 6/1999 | Ochs et al. | 132/321 |
| 2001/0024716 | A1 | * | 9/2001 | Chen et al. | 428/317.9 |

\* cited by examiner

Primary Examiner—John J. Wilson
Assistant Examiner—Robyn Kien Doan
(74) Attorney, Agent, or Firm—Christos S. Kyriakou; James B. Robinson

(57) ABSTRACT

The present invention provides a dental device that comprises a hemostatic agent and a method of making and using a dental device comprising a hemostatic agent.

7 Claims, No Drawings

Ing dental devices that comprise a hemostatic agent. In
HEMOSTAT COATED DENTAL FLOSS AND HEMOSTAT COATED DENTAL TAPE

FIELD OF THE INVENTION

The present invention pertains to the field of dental devices and more particularly, to dental floss and dental tape.

BACKGROUND OF THE INVENTION

Dental flosses have long been used to clean the spaces between the teeth and under the gum margin. One early example of a dental floss is described in U.S. Pat. No. 3,800,812. To increase the effectiveness of the floss, some flosses have included certain medicinal ingredients such as fluoride compounds to protect the tooth enamel from acid attack. Bactericides have also been used in connection with dental floss to inhibit periodontal disease.

When used properly, dental floss has been found to be effective in inhibiting tooth decay and gum disease and is recommended by dentists in the daily dental hygiene program. However, dental floss often causes the gums to bleed, which discourages its use by some people.

Attempts have been made to produce a superior dental floss that is convenient to use and is less prone to cause bleeding of the gums. One attempt to produce a dental floss that reduces gum bleeding is described in U.S. Pat No. 5,209,251. U.S. Pat. No. 5,209,251 describes a polytetrafluoroethylene dental floss having a low friction wax coating. Other dental flosses have been provided with a dentifrice component. For example, U.S. Pat. No. 3,830,246, U.S. Pat. No. 3,897,795, U.S. Pat. No. 4,215,478 and U.S. Pat. No. 3,771,536 describe dental flosses which are impregnated with a fluoride compound to aid in the delivery of the fluoride to the tooth surface between adjacent teeth. U.S. Pat. No. 4,033,365 describes a dental floss designed to retain flavorants over a long period of time through the use of non-wax polymeric coatings containing spray-dried flavor particles.

U.S. Pat. No. 3,943,949 describes a dental floss-like material in the form of a bundle of natural or synthetic fibers, such as nylon. The floss is coated with various waxes, including microcrystalline wax, to reduce the friction of the floss against the tooth surface. The wax coating is described as containing a spray-dried flavorant to be dispersed during use.

As exemplified by the above-noted patents, flossing is an extremely important adjunct to proper dental hygiene. Many of the dental flosses presently on the market have received limited consumer acceptance. The lack of consumer acceptance of any single dental floss in the market may be due at least in part to the propensity of dental floss to cause gingival bleeding. Dental floss is generally considered difficult and uncomfortable to use. Consumer dissatisfaction with dental flosses is frequently caused by the difficulty some consumers have in getting the floss into the tight spaces between teeth. The user must apply substantial downward force to pull the floss between the contact points of the teeth. The typical user will pull downward with sufficient force to allow the floss to pass between the teeth and snap against the gum surface, causing irritation and possible bleeding of the gum tissue. The difficulty in pulling the floss between the teeth is the result of the thickness of the floss compared to the spaces between the teeth. In order to reduce the risk of gum injury, many manufacturers have coated the floss with wax or other lubricant to reduce the friction coefficient and increase the ease with which it can be inserted between the teeth.

SUMMARY OF THE INVENTION

The present invention attempts to reduce the bleeding that occurs when consumers use such dental devices by providing dental devices that comprise a hemostatic agent. In certain embodiments, the dental device of the present invention is a dental floss or a dental tape comprising a hemostatic agent. In one desirable embodiment, the hemostatic agent is chitosan. Dental flosses and dental tapes of the present invention may be made from any of the materials that can be used to manufacture dental flosses or dental tapes, in particular commercially available polymers that are designed for such uses.

DETAILED DESCRIPTION OF THE INVENTION

Reference now will be made in detail to several embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment may be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In accordance with the present invention, it has been discovered that a dental device can be made that reduces bleeding by incorporating or otherwise including a hemostatic agent with the dental device. For example, a hemostatic agent may be impregnated in or coated onto a dental device. As used herein, hemostatic agents are substances or compounds that reduce or are capable of reducing bleeding and include, but are not limited to, such substances and compounds as oxidized cellulose, collagen, thrombin, fibrin and chitosan. One desirable hemostatic agent is chitosan. Desirable hemostatic agents includes chitosan, chitosan salts, derivative's of chitosan and mixtures thereof. Generally, chitosan is deacetylated chitin and is also known as β-1,4-poly-D25 glucosamine; poly-D-glucosamine; and poliglusam. Chitosan is a deacetylated product of chitin, an abundant natural glucosamine polysaccharide found in nature. In particular, chitin is found in the shells of crustaceans, such as crabs, lobsters and shrimp. Chitin is also found in the exoskeletons of marine zooplankton, in the wings of certain insects, such as butterflies and ladybugs, and in the cell walls of yeasts, mushrooms and other fungi.

On the structural level, chitosan is predominantly polyglucosamine, and is generally prepared by the alkaline hydrolysis of chitin. The degree of deacetylation normally ranges from about 70 to about 98 percent. The deacetylated amino groups are generally protonated at a pH of less than about 6, and therefore are responsible for positive charges, which make the chitosan polymer soluble in water. This characteristic also leads to high positive charge density in the chitosan compound. Chitosan generally dissolves in dilute solutions of organic acids such as formic, acetic, tartaric, and citric acids, and also in dilute mineral acids, except, for example, sulfuric acid. In general, the amount of acid required to dissolve chitosan is approximately stoichiometric with the amino groups. An excess of acid is acceptable, and in some cases, desirable.

The biocompatibility of chitosan administered orally and intravenously has been assessed in animals. In addition to being non-toxic, biocompatible and biodegradable, chitosan is also reported in the scientific literature to possess hemostatic, antimicrobial properties and other desirable biomedical properties. See for instance, *Rev. Macromol. Chem. Phys.*, C40, 69–83 (2000), *Chitin and Chitosan*, Editors, G. Skjak-Braek, T. Anthonsen and P. Sanford, Elsevier, (1988); and *Chitin in Nature and Technology*, Editors, R. Muzzarelli, C. Jeuniaux and G. W. Gooday, Plenum Press, (1986).

It is desirable that the hemostatic agent is at least partially soluble in water in order to facilitate processing and coating of the hemostatic agent onto the dental device. Advantageously, increased water solubility of the hemostatic agent increases the ability of the hemostatic agent to dissolve on contact with saliva and reduce bleeding. Desirable water-soluble hemostatic agents include, but are not limited to, various salts of chitosan including chitosan ascorbate and more particularly chitosan salts with carboxylic acids such as chitosan acetate, chitosan citrate, chitosan benzoate, chitosan nicotinate, chitosan malate, chitosan aspartate, chitosan glutamate, chitosan lactate, chitosan succinate, chitosan formate, chitosan pyruvate, chitosan propionate and chitosan tartrate. Other water-soluble hemostatic agents include carboxymethylcellulose salts such as sodium carboxymethylcellulose, and oxidized cellulose.

It is desirable that the hemostatic agent is impregnated in or coated on to the surface of a dental device in an "effective amount". An "effective amount" of hemostatic agent is an amount of hemostatic agent that must be present in or on the surface of a dental device in order to impart a demonstrable retardation of gum bleeding when the device is used. The effective amount will vary with the type, shape and size of the dental device, as well as the nature of the hemostatic agent. For example, it is desirable to have at least 0.1 milligrams of hemostatic agent per linear meter of dental floss or dental tape. It may be more desirable to have 0.5 milligrams of hemostatic agent per linear meter of dental floss or dental tape.

The hemostatic agent may reduce bleeding while remaining attached to the dental device (i.e., by contact with the affected area), or, more commonly, it may reduce bleeding once released from the device. The hemostatic agent may be released from the device by mechanical means or by dissolution in the aqueous environment of the mouth. For maximum effectiveness at controlling bleeding at and below the gingival margin, it is desirable that a hemostatic agent that may deposit between the teeth during flossing be at least partially water soluble in order to dissolve in the saliva and be redistributed to the gingival regions during and after flossing. When chitosan is used as the hemostatic agent, it may be desirable to use a preparation that dissolves rapidly, such as a high-density chitosan preparation called LIPOSAN ULTRA, available from Vanson, Incorporated of Redmond, Wash. High-density chitosan is described in U.S. Pat. No. 6,130,321, and is defined as chitosan having a tap density greater than 0.4 grams per milliliter. A fast-dissolving chitosan component simplifies the production process and may also increase the hemostatic performance of the product by hastening and increasing the total release of chitosan from the device into the mouth. Exemplary dental devices include devices for cleaning the spaces between teeth and include, but are not limited to, dental flosses and dental tapes. Dental flosses and dental tapes of the present invention may be manufactured by coating, impregnating or otherwise incorporating at least one hemostatic agent into or on the surface of the dental device. As used herein, the term "dental floss" also includes dental tapes and includes devices manufactured for use by consumers to clean the spaces between teeth. The form of the dental floss may include an individual fiber, bundles of fibers, tapes, and films.

Theoretically, any dental device can be coated or impregnated with a hemostatic agent in accordance with the present invention as long as the surface or the device or some component of the device is capable of receiving a hemostatic agent or has some affinity for a hemostatic agent or can be modified to receive a hemostatic agent. Dental flosses and dental tapes are readily and commercially available and can be used as a base material, i.e. dental device of the present invention. Most of these dental devices are made of synthetic or, occasionally, natural polymers and can be coated in accordance with at least one embodiment of the present invention. Surface modification, surfactants, wetting agents, emulsifiers, dispersing agents, viscosity modifiers and other additives and/or methods may be used to aid in the manufacture and coating of devices in accordance the present invention. Methods of coating are well known. Illustrative methods of coating a hemostatic agent onto the surface of a dental device are described in the examples below.

Dental flosses are more commonly used than dental tapes and can be coated with a hemostatic agent. Common dental floss substrate materials include such diverse polymer materials as polyamides such as nylon, fluorinated polymers such as polytetrafluoroethylene (PTFE), rayon, polyesters, acetate polymers, polyolefins, cotton, wool, silk and mixtures thereof. PTFE and polyamides such as nylon 6 and nylon 6,6 are three commonly used dental floss substrate materials.

Dental flosses and methods of making dental floss are well known. One example of a dental floss that may be used in accordance with the present invention is disclosed in U.S. Pat. No. 5,209,251 which is hereby specifically incorporated by reference herein in its entirety. The dental floss substrate used to prepare the floss of the present invention may be texturized. Dental tapes are also known and examples of dental tapes that may be used in accordance with the present invention are disclosed in U.S. Pat. No. 4,646,766 and U.S. Pat. No. 4,450,849 which are hereby specifically incorporated by reference herein in their entirety.

The dental flosses and dental tapes of the present invention may further comprise a coating composition or other composition or compound that serves to at least temporarily affix the hemostatic agent to the surface of the dental device or that increases the affinity of the hemostatic agent for the surface of the dental device. The coating composition may include any composition or substance that may be used to apply or otherwise help fix a hemostatic agent to the device including, but not limited to, water, solvents, diluents, viscosity modifiers, waxes, flavorants, surfactants, polymers, etc. It is understood that not all of the coating composition will be retained on the finished device and may evaporate upon drying. It is desirable that the coating, as well as the hemostatic agent, is at least partially water soluble so that the hemostatic agent can be coated without the use of nonaqueous solvents. It is even more desirable that at least an effective amount of the hemostatic agent and the coating composition, if needed, is soluble in water and saliva. Examples of suitable coating additives include, but are not limited to, polymers such as polyethyleneglycol, polyoxyethylene-polyoxypropylene block copolymers and mixtures thereof. Other coating additives include surfactants. Suggested commercial examples of suitable surfactants include, but are not limited to polysorbates such as TWEEN 80 and TMAZ 80.

A hemostatic agent may be applied to the floss material simultaneously with, subsequent to, or prior to the application of any coating additives. In addition to the hemostatic agent, dental devices in accordance with the present invention may also comprise one or more optional additives such as abrasives, anti-bacterial agents, antibiotics, anti-caries agents, antimicrobial agents, antioxidants, anti-plaque agents, cooling agents, desensitizers, flavorings, lubricants, remineralization agents, tartar control agents, and whitening agents. Suggested abrasives include, but are not limited to, silica and sodium bicarbonate. Suggested anti-bacterial agents include, but are not limited to, triclosan, thymol, eucalyptol, menthol, methyl salicylate, chlorhexidine, hexetidine, hydrogen peroxide and carbamide peroxide. Suggested anti-caries agents include, but are not limited to, triclosan, xylitol, and fluoride. Suggested anti-microbial agents include, but are not limited to, chlorhexidine and triclosan. Suggested anti-plaque agents include, but are not limited to, triclosan, menthol, thymol, eucalyptol, methyl salicylate and cetylpyridinium chloride. Suggested cooling agents, i.e., substances that provide a cooling effect upon dissolution include, but are not limited to, xylitol and menthol. Suggested whitening agents include, but are not limited to, hydrogen peroxide, carbamide peroxide and silica. Suggested flavoring agents include, but are not limited to, vanillin, peppermint oil, spearmint oil, wintergreen, menthol, carvone, anise oil, anethole, cinnamon, citrus oil, methyl salicylate, menthol, and thymol. Suggested remineralization agents include, but are not limited to, casein phosphopeptides, calcium phosphate, and calcium fluoride. Suggested tartar control agents include, but are not limited to, triclosan and fluoride.

The dental devices of the present invention may be made by applying a hemostatic agent in a liquid form or as part of an emulsion to a surface of a dental device.

The coating of a hemostatic agent onto a dental device may be in any form including, but not limited to, a film, a powder coating, droplets, waxes, a discontinuous coating, painted printed, etc. It is contemplated that a hemostatic agent may be part of a coating composition that includes a mixture of a hemostatic agent, a solvent and/or a carrier composition and optional adjuvants such as sweeteners, flavorings, abrasives, lubricants, anti-caries agents, antimicrobials, antibiotics, antioxidants, desensitizers, etc.

The coating composition may be prepared by melting a coating polymer and adding a hemostatic agent or by dissolving or emulsifying a hemostatic agent in a solvent, diluent, or other carrier such as water. For example, a tartar control agent or any other optional adjuvants may also be added to or otherwise included in the coating composition or coating solution. The coating composition may be applied to the dental floss or dental tape by unwinding a spool of a dental floss or tape substrate and passing it through a tank containing the coating composition. The coating composition is allowed to solidify or dry on the dental device after the coated dental device exits the coating tank. A dental device, such as floss or dental tape, now coated with a hemostatic agent and any optional ingredients, can be rewound onto a finished product spool.

Alternatively, a dental device in accordance with present invention may be made by coating the device with a coating composition containing a molten coating polymer absent any hemostatic agent. Prior to cooling and solidification, the coated device may be passed through or dusted with powdered hemostatic agent, whereby the agent would then become embedded in the molten coating composition. As yet another alternative method of making a dental device in accordance with the present invention, a dental device may be contacted with powdered hemostatic agent to pick up the agent as a powder dispersed within or on the surface of the dental device. The hemostatic agent may then be fixed onto the device by over-coating the device with the coating composition containing a coating polymer. To permit the hemostatic agent to migrate from its initial points of deposition on the teeth to the gingival margin during and after flossing, the coating composition should also be at least partially soluble in water to permit dissolution in the saliva. Suitable water soluble polymers useful as a component of a coating composition include, but are not limited to, polyethyleneglycols, polyoxyethylenepolyoxypropylene block copolymers and mixtures of these polymers. These polymers should preferably have a weight-average molecular weight of about 100 to about 20,000 g/mol, and more preferably, from about 800 to about 14,000 g/mol. The coating polymer should also desirably have a sufficiently high melting point so that it will solidify on the floss prior to re-rolling the coated floss on a take-up spool. Commercially available polymers that are suitable as a component of the coating compositions of the present invention include: PEG 32, sold under the tradename Carbowax by Union Carbide Corporation of Charleston, W.Va.; PEG 1450 also sold by Union Carbide Corporation of Charleston; W.Va.; and Poloxamer 407, sold under the tradename Pluronic F-127 by BASF of Edison, N.J. The first two polymers are polyethyleneglycols and the latter is a polyoxyethylene-polyoxypropylene block copolymer. Carbowax PEG 1450 has a weight average molecular weight of 1450, a melting point of 47° C., a viscosity of 30 centiStokes at 99° C. and a solubility in water of 70% by weight at 20° C. Pluronic F-127 has a weight average molecular weight of 12,600, a melting point of 56° C., a viscosity of 145 poise at 60° C. and a solubility in water of 10% by weight at a temperature of 20° C.

As previously stated, dental devices in accordance with the present invention may also contain one or more additional additives such as sweeteners, flavorings, abrasives, lubricants, anti-caries agents, antimicrobials, antibiotics, antioxidants and desensitizers. For example, a dental floss of the present invention may contain sodium fluoride as an anti-caries agent at a concentration of about 0.05 to about 2 mg per meter, desirably at a concentration of about 0.1 to about 1 mg per yard, and most desirably, at a concentration of about 0.2 to about 0.5 mg per meter in addition to the hemostatic agent.

The following examples describe various embodiments of the invention. Other embodiments within the scope of the claims herein will be apparent to one skilled in the art from consideration of the specification or practice of the invention as disclosed herein.

It is intended that the specification, together with the examples, be considered to be exemplary only, with the scope and spirit of the invention being indicated by the claims which follow the examples.

EXAMPLES

General Procedures

Examples of dental flosses comprising a chitosan containing coating were prepared. A few of the examples of dental floss were tested. The starting dental floss materials, i.e. the substrates, in the following examples are commercially available and conventional dental floss materials that are either based on nylon fibers or polytetrafluoroethylene (PTFE) fibers as noted. The chitosan used in the following examples was obtained from Vanson, Incorporated of Redmond, Wash. The citric acid used to form the chitosan citrate solutions in the following examples is a food grade citric acid and was obtained from the Archer Daniels Midland Company of Decatur, Ill.

In the examples, all percentages are given on a weight basis unless otherwise indicated. All molecular weights are given on a weight-average basis, unless otherwise noted.

Example 1

A hemostatic solution of 0.5 percent by weight of chitosan acetate in water, 0.5% w/w, was prepared by combining 1.0 gram of chitosan, in 200ml of a 1% aqueous solution of acetic acid.

Chitosan salt solutions can be prepared by dissolving a desired concentration of chitosan in an aqueous solution of a desired acid. A chitosan salt solution can be dried by various methods including lyophilization, spray drying or by heating in an oven. The resulting chitosan salt can then be dissolved in water to form a chitosan solution. It is understood that a chitosan salt solution, for example chitosan acetate, does not imply a covalent attachment of chitosan to acetate, but rather comprises a solution containing the acetate salt of chitosan.

Commercially available, conventional nylon dental floss was unwound and pulled through the 0.5% w/w solution of chitosan acetate at a rate of about 2 meters per minute. After immersion in the chitosan containing solution, the wet dental floss was run through a nip and then dried with blowing air to form a coating containing a hemostatic agent, e.g. chitosan, on the nylon dental floss. The hemostat coated floss was then wound. The hemostat coated floss can be packaged and is ready for use by a consumer.

Example 2

A second hemostatic solution of 2 percent by weight of chitosan citrate in water was prepared by combining and mixing 0.5 gram of chitosan (degree of deacetylation 78.8%), 0.56 gram of citric acid and 60 grams of distilled water. A conventional nylon dental floss was unwound and pulled through the solution of 2% w/w of chitosan citrate at a rate of about 10 meters per minute. After immersion in the solution, the wet dental floss was run through a nip and then dried with blowing air to form a chitosan coating on the nylon dental floss. The hemostat coated floss was then wound.

Example 3

A third hemostatic solution of 2 percent by weight of chitosan citrate and 2 percent by weight of TWEEN 80 in water was prepared. TWEEN 80 is poly(oxyethylene) sorbitan monooleate of 10 to 30 moles of ethylene oxide per mole. TWEEN 80 is commercially available from ICI Americas, Inc. of Wilmington, Del. Conventional PTFE dental floss was unwound and pulled through the chitosan citrate and TWEEN 80 solution. TWEEN 80 was included in the chitosan solution as a surfactant to assist the wetting of the chitosan solution on to the hydrophobic PTFE floss. After immersion, the floss was run through a nip, dried with blowing air and then wound.

Example 4

A fourth hemostatic coating solution was prepared by combining: 19.35 grams of distilled water; 0.117 grams of peppermint oil flavorant obtained from Global Essence, Inc. of Nutley, N.J.; 1.78 g of a 1 percent by weight solution of chitosan citrate in water; 0.117 grams of TMAZ 80, a polysorbate surfactant obtained from BASF, Inc. of Germany; and 2.00 grams of xylitol, a cooling agent obtained from Cultor of Finland. Conventional nylon dental floss was unwound and pulled through the hemostatic coating solution. After immersion, the floss was run through a nip, dried with blowing air, and then wound.

Example 5

A hemostatic coating solution was prepared by combining: 19.35 grams of distilled water; 0.117 grams of peppermint oil flavorant obtained from Global Essence, Inc. of Nutley, N.J.; 1.78 g of a 1 percent by weight solution of chitosan citrate in water; 0.117 grams of TMAZ 80, a polysorbate surfactant obtained from BASF, Inc. of Germany; and 2.00 grams of xylitol, a cooling agent obtained from Cultor of Finland. Conventional polytetrafluoroethylene dental tape was unwound and pulled through the hemostatic coating solution. After immersion, the dental tape was run through a nip, dried with blowing air, and then wound.

Example 6

A coating solution was prepared by combining: 58 grams of distilled water, 0.52 grams of peppermint oil flavorant, 1.4 grams of a 1 percent by weight solution of chitosan citrate in water, 2.0 grams of TMAZ 80 surfactant, and 2.1 grams of xylitol as a cooling agent. Conventional PTFE dental floss was unwound and pulled through the solution. After immersion, the floss was run through a nip and dried with blowing air to form a hemostat coated dental floss. The hemostat coated dental floss of this example was then wound and, ultimately, used in the conventional manner.

The hemostat coated floss of this Example no. 6 was tested in a side-by side comparison for performance against the conventional PTFE floss from which it was made. In the test, only one side of a subject's mouth was flossed with the hemostat coated floss formed in the process described above. The hemostat coated floss was used in a conventional flossing manner by a subject to floss the gaps between the seven teeth on the top half and the seven teeth on the bottom half on only one side of the subject's mouth. The conventional floss, from which the hemostat coated floss was made, was used to floss the gaps between the seven teeth on the top half and the seven teeth on the bottom half on the opposing side of the subject's mouth. The two gaps between the two middle teeth front teeth on the top half and on the bottom half of the subject were left unflossed.

After completing flossing on one side of the mouth, the subject spit into a glass of water, then rinsed the mouth several times using additional water, spitting the contents into the glass of water. After waiting 30 minutes, this entire process was repeated on the other side of the mouth using conventional PTFE floss. After waiting 30 minutes, the cycle was repeated, and ultimately four completed cycles of flossing and rinsing were performed on both sides of the mouth.

The flosses were also visually examined after flossing around each tooth. Bleeding was observed upon flossing with both the conventional and the hemostat coated flosses. However, the extent of bleeding was reduced with the hemostat-coated floss. The observed incidence of bleeding, as gauged by the number of times the floss showed discoloration, did not appear decreased when using the hemostat coated floss. However, the volume of blood decreased, supporting the conclusion that the hemostat-coated floss helps reduce the flow of blood.

Advantageously, the coated floss of the example also had greater friction against the fingers than the conventional PTFE floss from which it was made. This increased friction was not expected and facilitates efficient use of the floss. Specifically, the chitosan coated floss did not slide as much after being wrapped around a finger as did the conventional floss. Ultimately, a consumer will be required to use less "excess" floss to wrap around the fingers.

Example 7

A length of a conventional nylon dental floss was unwound and pulled through the coating solution of Example 7. The length of nylon dental floss was weighed before and after the coating process to determine whether the hemostat was coated onto the nylon floss and to determine how much of the hemostat was coated onto the floss. The length of nylon floss weighed 168.6 grams before being immersed in the coating solution. After immersion in the coating solution, the floss was run through a nip and dried with blowing air. The hemostat coated dental floss of this example was also air-dried for about 120 hours.

The hemostat coated, nylon dental floss of this example was weighed after the 120 hours of air drying. The hemostat coated dental floss had a final weight of 179.1 grams versus an initial uncoated weight of 168.6 grams, a 6.2 percent increase in mass as a result of absorbed coating.

Example 8

A length of a conventional PTFE dental floss was also unwound and pulled through the hemostatic solution of Example 8. The length of PTFE floss was weighed both before and after the coating process. The weight of the length of the conventional PTFE floss before immersion was 347.3 grams. After immersion in the hemostatic coating solution, the wet PTFE floss was run through a nip and dried with blowing air. The coated PTFE was also air-dried for 120 hours. The final weight of the hemostat coated PTFE dental floss was 354.5 grams versus an initial weight of 347.3 grams. The PTFE dental floss increased by 2.1 percent in mass as a result of the hemostatic coating process.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

In view of the above, it will be seen that the several advantages of the invention are achieved and other advantageous results obtained. As various changes can be made in the above methods and compositions without departing from the scope of the invention, it is intended that all matter contained in the above description shall be interpreted as illustrative and not in a limiting sense. These and other modifications and variations to the present invention may be practiced by those of ordinary skill in the art, without departing from the spirit and. scope of the present invention, which is more particularly set forth in the appended claims. In addition, it should be understood that aspects of the various embodiments may be interchanged both in whole and in part. Furthermore, those of ordinary skill in the art will appreciate that the above description is by way of example only, and is not intended to limit the invention so further described in such appended claims. Therefore, the spirit and scope of the appended claims should not be limited to the description of the embodiments contained therein.

What is claimed is:

1. A dental floss comprising a hemostatic agent selected from the group consisting of chitosan, chitosan salts, derivatives of chitosan and chitosan salts and chitosan containing compounds.

2. The dental floss or tape of claim 1 wherein the hemostatic agent comprises a chitosan salt.

3. The dental floss or tape of claim 1 wherein the hemostatic agent comprises high-density chitosan.

4. The dental floss of claim 2 wherein the chitosan salt comprises an anionic component selected from the group consisting of citrate, benzoate, ascorbate, acetate, nicotinate, malate, lactate, succinate, pyruvate, aspartate, glutamate and tartrate.

5. The dental floss of claim 2 wherein the chitosan salt is chitosan citrate, chitosan benzoate or chitosan acetate.

6. The dental floss of claim 1 wherein the hemostatic agent is at least partially soluble in water.

7. A method of making a dental floss comprising the steps of: providing a hemostatic agent selected from the group consisting of chitosan, chitosan salts and derivatives thereof; dissolving said hemostatic agent in an aqueous solution to produce a chitosan solution; contacting a dental floss or tape with the hemostatic agent in liquid form; and drying the hemostatic agent on the dental floss or tape substrate.

* * * * *